US006867023B2

(12) United States Patent
Honma et al.

(10) Patent No.: US 6,867,023 B2
(45) Date of Patent: Mar. 15, 2005

(54) PRODUCTION METHOD OF POLYHYDROXYALKANOATE FROM SUBSTITUTED FATTY ACID ESTER AS RAW MATERIAL

(75) Inventors: Tsutomu Honma, Kanagawa (JP); Tetsuya Yano, Kanagawa (JP); Takeshi Imamura, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 317 days.

(21) Appl. No.: 09/984,437

(22) Filed: Oct. 30, 2001

(65) Prior Publication Data

US 2002/0081646 A1 Jun. 27, 2002

(30) Foreign Application Priority Data

Oct. 30, 2000 (JP) ........................................ 2000-330721

(51) Int. Cl.$^7$ ................................................ C12P 7/62
(52) U.S. Cl. ........................ 435/135; 435/244; 435/170; 435/169; 435/171; 435/253.3; 435/252.1
(58) Field of Search ................................. 435/135, 244, 435/170, 169, 141, 253.8, 252.1

(56) References Cited

U.S. PATENT DOCUMENTS

| 4,393,167 | A |   | 7/1983  | Holmes et al. | ............... | 525/64  |
|-----------|---|---|---------|---------------|----------------|---------|
| 4,477,654 | A | * | 10/1984 | Holmes et al. | ............. | 528/361 |
| 4,876,331 | A |   | 10/1989 | Doi           | ............. | 528/361 |
| 5,292,860 | A |   | 3/1994  | Shiotani et al. | ............. | 528/361 |
| 5,334,698 | A |   | 8/1994  | Witholt et al. | ............... | 528/354 |
| 5,485,248 | A |   | 1/1996  | Yano et al.   | ................. | 355/206 |
| 6,521,429 | B2 | * | 2/2003 | Honma et al.  | ............... | 435/135 |

FOREIGN PATENT DOCUMENTS

| JP | 5-93049   | 4/1993  |
|----|-----------|---------|
| JP | 5-223513  | 8/1993  |
| JP | 6-15604   | 3/1994  |
| JP | 7-14352   | 2/1995  |
| JP | 7-265065  | 10/1995 |
| JP | 8-19227   | 2/1996  |
| JP | 2642937   | 5/1997  |
| JP | 9-191893  | 7/1997  |

OTHER PUBLICATIONS

Kim, O, et al., "Bioengineering of poly(β–hydroxyalkanoates) for advanced material applications: incorporation of cyano and nitrophenoxy side chain substituents", Can. J. Microbiol., vol. 41, (Suppl. 1), 1995, pp. 32–43.

Ritter, H., et al., "Bacterial production of polyesters bearing phenoxy groups in the side chains, 1 Poly(3–hydroxy–5–phenoxypentanoate–co–3–hydroxy–9–phenoxy–nonanoat ) from *Pseudomonas oleovorans*", Macromolecular Chemistry and Physics, vol. 195, No. 5, May 1994, pp. 1665–1672.

Gross, Richard, A., et al., "Biosynthesis and Characterization of Poly(β–hydroxyalkanoates) Produced by *Pseudomonas oleovorans*", Amer. Chem. Soc., vol. 2, 1989, pp. 1106–1115.

Lageveen, R.G., et al., Formation of Polyesters by *Pseudomonas oleovorans*: Effect of Substrates on Formation and Composition of Poly–(R)–3–Hydroxyalkanoates and Poly–(R)–3–Hydroxyalkenoates, Applied and Environmental Microbiology, vol. 54, No. 12, Dec. 1, 1988, pp. 2924–2932.

Hazer, B. et al., "Bacterial production of poly–3–hydroxyalkonoates containing arylalkyl substituent groups", Polymer, vol. 37, No. 26, Dec. 1, 1996, pp. 5951–5957.

Steinbuechel, A., et al., "Diversity of bacterial polyhydroxyalkanoic acids", FEMS Microbiol. Letters, vol. 128, No. 3, May 15, 1995, pp. 219–228.

Antoun, et al., "Production of a Chiral Polyester by *Pseudomonas oleovorans* Growth With 5–Phenyl–2,4–Pentadienoic Acid"; Chiralty, vol. 3, No. 6, 492–494 (1991).

Kim, et al.; Preparation and Characterization of Poly (β–hydroxyalkanoates) Obtain d from *Pseudomonas oleovorans* Grown with Mixtures of 5–Phenylvaleric Acid and n–Alkanoic Acids; Macromolecules, vol. 24, No. 19, 5256–5260, 1991.

Kim, et al.; "OPTO–Active Polymers Obtained by Microbial Transformations"; Polym r Preprint, 35, 627–628, 1994.

Fritzsch , t al; "An unusual bact rial poly st r with a ph nyl p ndant group"; Makromol. Ch m. *191*, 1957–1965, (1990).

* cited by examiner

*Primary Examiner*—Irene Marx
(74) *Attorney, Agent, or Firm*—Fitzpatrick, Cella, Harper & Scinto

(57) ABSTRACT

Polyhydroxyalkanoates comprising a monomer unit having the following chemical formula (2):

$$\begin{array}{c} R \\ | \\ (CH_2)_x \\ | \\ -\!\!\!-\!\!(CH\!-\!CH_2\!-\!\overset{O}{\underset{\|}{C}}\!-\!O)\!\!-\!\!\!- \end{array} \quad (2)$$

(where the reference characters R represents an arbitrarily selected substituent and x represents an integer of 0 to 8) is produced by culturing a microorganism in a culture medium containing a substituted fatty acid ester having the following chemical formula (1):

$$R\!-\!(CH_2)_{x+2}\!-\!\overset{O}{\underset{\|}{C}}\!-\!OR' \quad (1)$$

(where the reference characters R and R' separately denote an optional substituent and x represents an integer of 0 to 8). The microorganism is capable of taking the substituted fatty acid ester into the cells and synthesizing the desired polyhydroxyalkanoate in the culture medium.

11 Claims, No Drawings

PRODUCTION METHOD OF POLYHYDROXYALKANOATE FROM SUBSTITUTED FATTY ACID ESTER AS RAW MATERIAL

BACKGROUND OF THE INVENTION

1. Field of the Invention

The present invention relates a method of efficiently producing polyhydroxyalkanoates (hereinafter abbreviated as PHAs) by means of microorganisms. More particularly, the present invention relates to a method of producing PHAs having a desired chemical structure, efficiently as compared with conventional methods, from substituted fatty acid esters as a raw material by using microorganisms capable of producing PHAs having a substituent derived from the raw material in a side chain and accumulating it in their cells.

2. Related Background Art

Many microorganisms have already been reported to produce poly(3-hydroxybutyric acid) (hereinafter abbreviated as PHB) or other PHAs and to accumulate those products in their cells (Biodegradable Plastics Handbook, edited by Biodegradable Plastics Society, published by NTS, pp.178–197). Like conventional plastics, those polymers can be utilized in production of a variety of products through melt processing or the like. Further owing to the biodegradability, those polymers have the advantage that they can completely be decomposed by microorganisms in nature. Consequently, unlike many conventionally used synthesized polymer compounds, they do not remain in the natural environments to cause pollution, nor need to be incinerated, and therefore they are advantageous in terms of prevention of air pollution and global warming. Further, they have an excellent biocompatibility and are highly expected to be used as soft materials for medical use.

It has been well-known that the microorganism-produced PHAs may have a variety of compositions and structures depending on the types of microorganisms used for the production as well as and the compositions of the culture media and the conditions for culturing them, and mainly from a viewpoint of improving the physical properties of PHAs, investigations have been performed regarding how to control the compositions and structures.

For example, it has been reported that Alcaligenes eutrophus H16, ATCC NO. 17699 and its mutant strains produce copolymers of 3-hydroxybutyric acid (hereinafter abbreviated as 3HB) and 3-hydroxyvaleric acid (hereinafter abbreviated as 3HV) in various composition ratios by changing the carbon sources in their culture (Japanese Patent Publication No. 6-15604, Japanese Patent Publication No. 7-14352, Japanese Patent Publication No. 8-19227 and the like).

Further, Japanese Patent Application Laid-Open No. 9-191893 discloses that Comamonas acidovorans IFO 13852 produces a polyester comprising 3HB and 4-hydroxybutyric acid as monomer units by culturing with gluconic acid and 1,4-butanediol as carbon sources.

Incidentally, PHAs disclosed in these documents are referred to as 'usual' PHA because of having no side chain other than methylene or ethylene side chains.

On the other hand, Japanese Patent gazette No. 2642937 discloses that Pseudomonas oleovorans ATCC 29347 produces PHAs comprising monomer units of 3-hydroxyalkanoates (hereinafter abbreviated as 3HAs) of 6 to 12 carbon atoms by supplying acyclic aliphatic hydrocarbons as carbon sources.

Japanese Patent Application Laid-Open No. 5-74492 discloses a method for producing copolymers of 3HB and 3HV by bringing microorganisms, Methylobacterium sp., Paracoccus sp., Alcaligenes sp., and Pseudomonas sp. into contact with primary alcohols of 3 to 7 carbons.

Japanese Patent Laid-Open No. 5-93049 and Japanese Patent Laid-Open No. 7-265065 disclose that binary copolymers of 3HB and 3-hydroxyhexanoic acid (hereinafter abbreviated as 3HHx) are produced by culturing Aeromonas caviae in oleic acid or olive oil as carbon sources.

Further, certain types of microorganisms are reported to produce PHAs into which a variety of substituents including, for example, unsaturated hydrocarbons, ester group, allyl group, cyano group, halogenated hydrocarbons, epoxide and the like are introduced, and it has been tried to improve the physical properties of microorganism-produced PHAs by employing such a technique.

For example, Makromol. Chem., 191, 1957–1965, 1990, Macromolecules, 24, 5256–5260, 1991, Chirality, 3, 492–494, 1991, and the like report that Pseudomonas oleovorans produces PHAs containing 3-hydroxy-5-phenylvaleric acid (hereinafter abbreviated as 3HPV) as a monomer unit and some changes in the polymer physical properties are found, which are attributable to the fact that 3HPV is contained.

Incidentally, PHAs having side chains as disclosed in these documents are referred to as 'unusual' PHAs in this specification.

Conventionally, microorganism-produced PHAs having a variety of compositions and structures have been obtained by changing the types of microorganisms to be employed for the production, the culture compositions and the culturing conditions. The purposes of the trials are mainly to improve the physical properties of PHAs as plastics by changing the ratios of a plurality of 3HAs contained in the PHAs.

On the other hand, the unusual PHAs into which substituent groups are introduced into their side chains as described above are expected to be developed for wide applications as functional polymers having remarkably useful, functional properties attributed to the characteristics of the introduced substituents. It is therefore supposed to be extremely useful and important to develop innovative polymers provided with such functional properties in addition to the biodegradability, microorganisms capable of producing and internally accumulating such polymers, and efficient production methods of such polymers using such microorganisms.

Incidentally, the methods generally employed for producing such unusual PHAs into which a variety of substituent groups are introduced as side chains, that is, PHAs containing monomer units represented by the following chemical formula (2), by microorganisms, comprise steps of chemically synthesizing a substituted fatty acid having the following chemical formula (6) having the substituent to be introduced, culturing microorganisms in the synthesized fatty acid, and then extracting the produced PHA, as the above reported examples using Pseudomonas oleovorans.

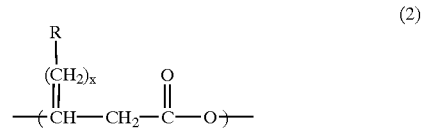

(wherein R represents an arbitrarily selected substituent and x represents an integer of 0 to 8.)

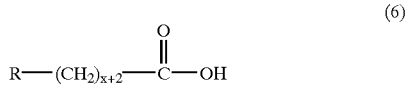

(wherein R represents an arbitrarily selected substituent and x represents an integer of 0 to 8.)

For example, Polymer Prepr., 35, 627–628, 1994 and Can. J. Microbiol., 41, 32–43, 1995 report that PHAs were produced by the method illustrated in the following reaction scheme.

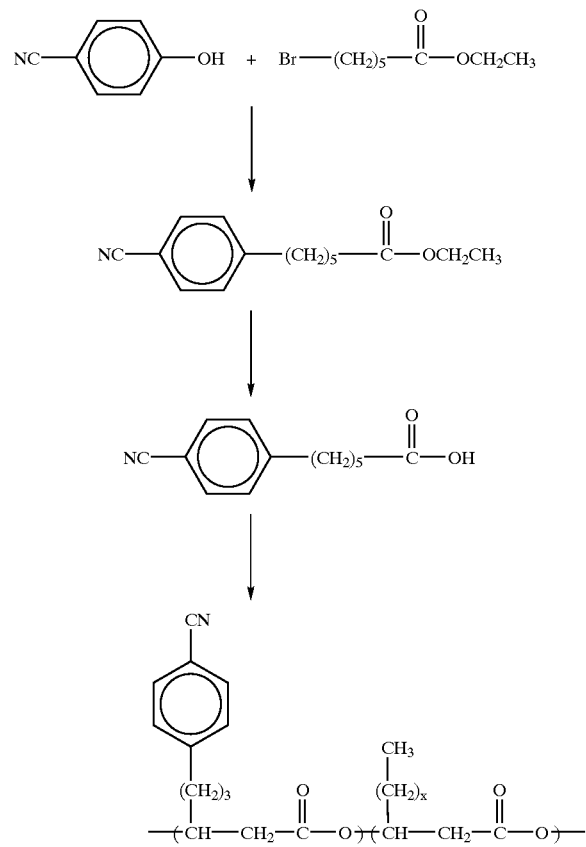

(wherein x represents 2 or 4.)

That is, at first, 6-(4-cyanophenoxy)hexanoic acid ethyl ester is synthesized by Williamson reaction of 4-cyanophenol and 6-bromohexanoic acid ethyl ester. Then, the 6-(4-cyanophenoxy)hexanoic acid ethyl ester is hydrolyzed under an alkaline condition to obtain 6-(4-cyanophenoxy)hexanoic acid. Finally, the obtained 6-(4-cyanophenoxy)hexanoic acid is supplied to *Pseudomonas oleovorans*, which is one of PHA producing bacteria, to culture the bacterium and the product is extracted to obtain a PHA containing 3-hydroxy-6-(4-cyanophenoxy)hexanoic acid as a monomer unit.

However, in the general production methods of the unusual PHAs involving steps of chemically synthesizing a substituted fatty acid and supplying it to microorganisms as described above, the chemical synthesis of the raw materials, i.e. the substituted fatty acids, requires several steps of chemical reactions to result in considerably complicated steps for the production and in many cases, it takes a long time, costs a great expense and requires troublesome works. Further, depending on the types, the number, and the loci of the substituents, there possibly exists a trouble such that the hydrolytic decomposition reaction of an ester does not smoothly proceed in the synthesizing process of the substituted fatty acid, which has posed various problems in the unusual PHA production in industrial scale and in the apparatus development for the production.

SUMMARY OF THE INVENTION

The inventors have enthusiastically made investigations to develop a PHA production method for microbiologically producing unusual PHAs by using raw materials which are relatively easily synthesized or got as compared with the substituted fatty acids. As a result, the inventors have found that desired unusual PHAs can efficiently be obtained by using a culture medium containing a substituted fatty acid ester having the following chemical formula (1), which is an intermediate in the chemical synthesis process for a substituted fatty acid, a conventional raw material, and which is easily synthesized with a higher degree of freedom as compared with the substituted fatty acid, for culturing microorganisms and thus completed the present invention.

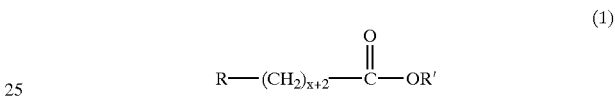

(wherein R and R' represent an arbitrarily selected substituent and x represents an integer of 0 to 8.)

That is, the invention is a method for producing a PHA having a monomer unit represented by the above chemical formula (2), which comprises a step of culturing microorganisms capable of taking a substituted fatty acid ester having the above chemical formula (1) in their cells and synthesizing the PHA in a culture medium containing the substituted fatty acid ester.

Further, the invention relates to a method of producing the above-described PHA further comprising a step of isolating the PHA produced by the microorganisms.

Incidentally, the microorganisms having the capability of producing and internally accumulating the PHA are preferably selected from microorganisms belonging to *Pseudomonas* sp. For example, the use of at least one strain selected from *Pseudomonas cichorii* YN2, *Pseudomonas cichorii* H45, or *Pseudomonas jessenii* P161 is particularly preferred.

DESCRIPTION OF THE PREFERRED EMBODIMENTS

As the substituted fatty acid ester to be used for the method of the invention, any compound having the chemical formula (1) may be used without particular restrictions as long as it is usable as a raw material for the unusual PHA production by microorganisms and typical examples includes fatty acids comprising a functional group such as phenyl, phenoxy, benzoyl, cyclohexyl, thienyl and the like which may be chemically modified in a variety of manners at some loci. Specific compounds to be preferably used include substituted fatty acid esters such as 5-phenylvaleric acid methyl ester, 5-(4-fluorophenyl) valeric acid methyl ester, 6-phenylhexanoic acid methyl ester, 4-phenoxy-n-butyric acid methyl ester, 4-(3-fluorophenoxy)-n-butyric acid methyl ester, 4-(4-fluorophenoxy)-n-butyric acid methyl ester, 4-(4-cyanophenoxy)-n-butyric acid methyl ester, 4-(4-nitrophenoxy)-n-butyric acid methyl ester, 5-phenoxyvaleric acid methyl ester, 5-(4-fluorophenoxy) valeric acid methyl ester, 5-benzoylvaleric acid methyl ester, 4-cyclohexylbutyric acid methyl ester, 5-(2-thienyl)valeric acid methyl ester, 5-phenylvaleric acid ethyl ester, 5-(4-fluorophenyl)valeric acid ethyl ester, 6-phenylhexanoic acid ethyl ester, 4-phenoxy-n-butyric acid ethyl ester, 4-(3-fluorophenoxy)-n-butyric acid ethyl ester, 4-(4-fluorophenoxy)-n-butyric acid ethyl ester, 4-(4-cyanophenoxy)-n-butyric acid ethyl ester, 4-(4-nitrophenoxy)-n-butyric acid ethyl ester, 5-phenoxyvaleric acid ethyl ester, 5-(4-fluorophenoxy)valeric acid ethyl ester, 5-benzoylvaleric acid ethyl ester, 4-cyclohexylbutyric acid ethyl ester, 5-(2-thienyl)valeric acid ethyl ester, etc.

Hereinafter, the microorganisms and the culturing process to be employed for the invention are described.

(Microorganism)

To be employed for the method of the invention are microorganisms having capability of producing PHAs containing a monomer unit having the chemical formula (2) using the substituted fatty acid esters having the chemical formula (1) as a raw material (a substrate) and examples thereof include PHA-producing microorganisms as described in Japanese Patent Application No. 11-371863, i.e., *Pseudomonas cichorii* YN2, *Pseudomonas cichorii* H45, and *Pseudomonas jessenii* P161. Incidentally, the YN2 strain, the H45 strain, and the P161 strain were deposited, with domestic deposition numbers FERM P-17411, FERM P-17410, and FERM P-17445, respectively, in National Institute of Bioscience and Human-technology (Depository for Patent Microorganisms), Agency of Industrial Science and Technology, MITI, located at AIST Tsukuba Central 6, 1-1-1 Higashi, Tsukuba, Ibaraki, Japan, and were given international accession numbers FERM BP-7375, FERM BP-7374, and FERM BP-7376, respectively, under the Budapest Treaty. The YN2 strain and the H45 strain were deposited on Jun. 3, 1999, and the P161 strain was deposited on Jul. 1, 1999.

The bacteriological properties of the above-described H45 strain, YN2 strain, and P161 strain are as follows.

<Bacteriological properties of H45 strain>
(1) Morphological properties

| | |
|---|---|
| Cell shape and size: | rod, 0.8 μm × (1.0 to 1.2) μm |
| Pleomorphism: | none |
| Mobility: | motile |
| Spore formation: | none |
| Gram staining: | negative |
| Colony shape: | circular, smooth in entire rim, low convex shape, smooth in surface layer, luster, cream color |

(2) Physiological properties

| | |
|---|---|
| Catalase: | positive |
| Oxydase: | positive |
| O/F test: | oxidation type |
| Nitrate reduction: | negative |
| Indole production: | negative |
| Glucose acidification: | negative |
| Arginine dihydrolase: | negative |
| Urease: | negative |
| Esculin hydrolysis: | negative |
| Gelatin hydrolysis: | negative |
| β-galactosidase: | negative |
| Fluorescent pigment production on King's B agar: | positive |
| Growth on 4% NaCl: | negative |
| Accumulation of poly-β-hydroxybutyric acid: | negative |

(3) Substrate assimilation

| | |
|---|---|
| Glucose: | positive |
| L-arabinose: | negative |
| D-mannose: | positive |
| D-mannitol: | positive |
| N-acetyl-D-glucosamine: | positive |
| Maltose: | negative |
| Potassium gluconate: | positive |
| n-capric acid: | positive |
| Adipic acid: | negative |
| dl-malic acid: | positive |
| Sodium citrate: | positive |
| Phenyl acetate: | positive |

<Bacteriological properties of YN2 strain>
(1) Morphological properties

| | |
|---|---|
| Cell shape and size: | rod, 0.8 μm × (1.5 to 2.0) μm |
| Pleomorphism: | none |
| Mobility: | motile |
| Spore formation: | none |
| Gram staining: | negative |
| Colony shape: | circular, smooth in entire rim, low convex shape, smooth in surface layer, luster, semi-transparent |

(2) Physiological properties

| | |
|---|---|
| Catalase: | positive |
| Oxydase: | positive |
| O/F test: | oxidation type |
| Nitrate reduction: | negative |
| Indole production: | positive |
| Glucose acidification: | negative |
| Arginine dihydrolase: | negative |
| Urease: | negative |
| Esculin hydrolysis: | negative |
| Gelatin hydrolysis: | negative |
| β-galactosidase: | negative |
| Fluorescent pigment production on King's B agar: | positive |
| Growth on 4% NaCl: | positive (weak growth) |
| Accumulation of poly-β-hydroxybutyric acid: | negative |
| Hydrolysis of Tween 80: | positive |

(3) Substrate assimilation

| | |
|---|---|
| Glucose: | positive |
| L-arabinose: | positive |
| D-mannose: | negative |
| D-mannitol: | negative |
| N-acetyl-D-glucosamine: | negative |
| Maltose: | negative |
| Potassium gluconate: | positive |
| n-capric acid: | positive |
| Adipic acid: | negative |
| dl-malic acid: | positive |
| Sodium citrate: | positive |
| Phenyl acetate: | positive |

<Bacteriological properties of P161 strain>
(1) Morphological properties

| | |
|---|---|
| Cell shape and size: | spherical, ∅0.6 μm, rod, 0.6 μm × (1.5 to 2.0) μm |
| Pleomorphism: | found (elongation type) |
| Mobility: | motile |
| Spore formation: | none |
| Grain staining: | negative |
| Colony shape: | circular, smooth in entire rim, low convex shape, smooth in surface layer, pale yellow color |

(2) Physiological properties

| | |
|---|---|
| Catalase: | positive |
| Oxydase: | positive |
| O/F test: | oxidation type |
| Nitrate reduction: | positive |
| Indole production: | negative |
| Glucose acidification: | negative |
| Arginine dihydrolase: | positive |
| Urease: | negative |
| Esculin hydrolysis: | negative |
| Gelatin hydrolysis: | negative |

-continued

| | |
|---|---|
| β-galactosidase: | negative |
| Fluorescent pigment production on King's B agar: | positive |
| (3) Substrate assimilation | |
| Glucose: | positive |
| L-arabinose: | positive |
| D-mannose: | positive |
| D-mannitol: | positive |
| N-acetyl-D-glucosamine: | positive |
| Maltose: | negative |
| Potassium gluconate: | positive |
| n-capric acid: | positive |
| Adipic acid: | negative |
| dl-malic acid: | positive |
| Sodium citrate: | positive |
| Phenyl acetate: | positive |

Further, in addition to microorganisms belonging to the *Pseudomonas* sp., it is also possible to use microorganisms belonging to *Aeromonas* sp., *Comamonas* sp., *Burkholderia* sp. and the like and capable of producing PHAs containing a monomer unit having the chemical formula (2) using a substituted fatty acid ester having the chemical formula (1) as a raw material (substrate).

(Culturing Process)

For culturing microorganisms to be employed in the production method of PHA according to the invention, for example, for preparation of a stock culture and cultivation for reliably retaining the number of bacteria and the active state necessary to produce PHAs, culture media containing components required for growth of the microorganisms are properly selected to be employed. For example, in the case of normal growth of microorganisms, any types of culture media such as commonly used natural culture media (nutrient broth, L-broth and the like), artificial culture media such as containing nutrients and the like can be used unless they have adverse effects on the growth and survival of the microorganisms. Culturing conditions such as temperature, airation, stirring and the like may properly be selected depending on the microorganisms.

In the case of producing and accumulating PHAs containing a monomer unit having the chemical formula (2) using the above microorganisms, a two-step culturing method can be used, comprising a first step of culturing the microorganisms in an inorganic culture medium containing substituted fatty acid esters having the chemical formula (1), microorganism growth substrates such as glucose, polypeptone, yeast extract and the like until the culture reaches from the logarithmic phase to the stationary phase and then recovering the bacterial cells by centrifugal separation and a second step of further culturing them in an inorganic culture medium which contains substituted fatty acid esters having the chemical formula (1) and the above growth substrates but is restricted in the inorganic nitrogen source. On the other hand, a one-step culturing method can also be used, comprising a step of culturing in an inorganic culture medium containing substituted fatty acid esters having the chemical formula (1) and the above growth substrates until the culture reaches from the logarithmic phase to the stationary phase.

As inorganic culture media to be used for the above-described culturing method, any kinds of culture media can be used if it contains components with which the subject microorganisms can grow, such as a phosphorus source (e.g., phosphoric acid salts), an inorganic nitrogen source (e.g., ammonium salts, nitric acid salts and the like). Examples thereof include an MSB culture medium, an M9 culture medium. Incidentally, the composition of the M9 culture medium employed in the examples of the invention is as follows.

| | |
|---|---|
| $Na_2HPO_4$: | 6.2 g |
| $KH_2PO_4$: | 3.0 g |
| NaCl: | 0.5 g |
| $NH_4Cl$: | 1.0 g |

(per 1 l of the culture medium, pH 7.0)

Further, the concentration of the substituted fatty acid ester as a raw material to be added to the culture medium may properly be selected corresponding to the types of the strains of the microorganism, the density of the bacterial cells, or the culture method and generally it is preferable to be selected within 0.01% to 0.5% of the content in the culture medium. Incidentally, in the above-described two-step culturing method, culturing may be carried out without adding the substituted fatty acid ester at the time of the first-step culture.

Additionally, in the case of adding a growth substrate of microorganism such as glucose, fructose, mannose, polypeptone, yeast extract and the like, their concentration may properly be selected depending on the types of the microorganisms, the density of the bacterial cells, or the culturing method and generally, the content in the culture medium may be selected within a range from about 0.1% to 1.0%. Incidentally, in the above-described two-step culturing method, culturing may be carried out without adding the growth substrate at the time of the second-step culturing.

Any method applicable for a common microorganism culture, e.g., a batch type culture, a fluidized batch type culture, a continuous culture, a reactor type culture, a solid culture, and the like may be employed. The culture temperature at that time may properly be selected depending on the types of the microorganisms, the density of the bacterial cells, or the culturing method and generally, and it is preferably to keep in a range within which the microorganism to be used can be grown and propagated, for example, at 14° C. to 40° C., preferably 20° C. to 35° C.

The recovery of PHAs from the bacterial cells of the microorganism in the invention, commonly carried out extraction with an organic solvent such as chloroform is simplest, however, in the environments where an organic solvent is unsuitable to be used, a method for removing the bacterium cell components by treatment with surfactants such as SDS, enzymes such as lysozyme, and chemical agents such as EDTA, sodium hypochlorite, ammonia and the like and then recovering PHAs can be used.

Incidentally, culture of microorganism of the invention, production of PHA by microorganism of the invention, and accumulation in the bacterial cells as well as recovery of PHA from the bacterial cells in the invention are not restricted to the foregoing practically exemplified methods.

EXAMPLES

Hereinafter, a PHA production method will be described more particularly by illustrating practical examples. Although these practical examples are those of most preferred embodiments of the invention, the invention is not at all restricted to these practical examples.

Example 1

Each one strain selected from *Pseudomonas cichorii* YN2, *Pseudomonas cichorii* H45, and *Pseudomonas jess-* enii P161 was inoculated into 200 mL of a M9 culture medium containing 0.5% of D-glucose and 0.1% of 5-phenylvaleric acid methyl ester and cultured at 30° C. with shaking at 125 strokes/minute, and after 66 hours, bacterial cells were recovered by centrifugation, re-suspended in 200 mL of a M9 culture medium containing 0.5% of D-glucose and 0.1% 5-phenylvaleric acid methyl ester and not containing inorganic nitrogen source (NH$_4$Cl) and cultured at 30° C. with shaking at 125 strokes/minute. After 44 hours, the bacterial cells were recovered by centrifugal separation, washed once with cold methanol and then freeze-dried.

The resulting freeze-dried pellet was suspended in 20 mL of chloroform and stirred at 60° C. for 24 hours to extract PHA. After being filtered through a membrane filter of 0.45 μm pore diameter, the extracted solution was concentrated by a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass analyzer (GC-MS, Shimadzu QP-5050, EI method) to identify the methyl ester of the PHA monomer unit. As a result, as shown in Table 1, it was confirmed that PHA containing 3-hydroxy-5-phenylvaleric acid as a monomer unit was produced.

TABLE 1

| Strain | YN2 | H45 | P161 |
|---|---|---|---|
| Cell dried weight (mg/L) | 202 | 323 | 246 |
| Polymer dried weight (mg/L) | 49 | 104 | 67 |
| Polymer dried weight/cell dried weight | 24% | 32% | 27% |
| Monomer unit composition(GC-MS: TIC peak area ratio) | | | |
| 3-hydroxybutyric acid | 2% | 0% | 35% |
| 3-hydroxyoctanoic acid | 1% | 2% | 1% |
| 3-hydroxydecanoic acid | 3% | 2% | 3% |
| 3-hydroxydodecanoic acid | 1% | 1% | 0% |
| 3-hydroxydodecenoic acid | 2% | 1% | 0% |
| 3-hydroxy-5-phenylvaleric acid | 91% | 94% | 61% |

Example 2

Each one strain selected from *Pseudomonas cichorii* YN2, *Pseudomonas cichorii* H45, and *Pseudomonas jessenii* P161 was inoculated into 200 mL of a M9 culture medium containing 0.5% of D-glucose and 0.01% of 5-phenylvaleric acid methyl ester and cultured at 30° C. with shaking at 125 strokes/minute, and after 46 hours, the bacterial cells were recovered by centrifugal separation, suspended again in 200 mL of a M9 culture medium containing 0.5% of D-glucose, 0.1% of 5-phenylvaleric acid methyl ester and not containing inorganic nitrogen source (NH$_4$Cl) and cultured at 30° C. with shaking at 125 strokes/minute, and after 41 hours, the bacterial cells were recovered by centrifugal separation, washed once with cold methanol and then freeze-dried.

The resulting freeze-dried pellets were suspended in 20 mL of chloroform and stirred at 60° C. for 24 hours to extract PHA. After being filtered through a membrane filter of 0.45 μm pore diameter, the extracted solution was concentrated in a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass spectrum analyzer (GC-MS, Shimadzu QP-5050, EI method) to identify the methyl ester of the PHA monomer unit. As a result, as shown in Table 2, it was confirmed that PHA containing 3-hydroxy-5-phenylvaleric acid as a monomer unit was produced.

TABLE 2

| Strain | YN2 | H45 | P161 |
|---|---|---|---|
| Cell dried weight (mg/L) | 856 | 819 | 369 |
| Polymer dried weight (mg/L) | 296 | 268 | 159 |
| Polymer dried weight/cell dried weight | 35% | 33% | 43% |
| Monomer unit composition(GC-MS: TIC peak area ratio) | | | |
| 3-hydroxybutyric acid | 1% | 0% | 6% |
| 3-hydroxyhexanoic acid | 0% | 0% | 1% |
| 3-hydroxyoctanoic acid | 2% | 2% | 5% |
| 3-hydroxydecanoic acid | 4% | 4% | 9% |
| 3-hydroxydodecanoic acid | 2% | 2% | 4% |
| 3-hydroxydodecenoic acid | 2% | 2% | 5% |
| 3-hydroxy-5-phenylvaleric acid | 89% | 90% | 70% |

Example 3

*Pseudomonas cichorii* YN2 was inoculated into 200 mL of a M9 culture medium containing 0.5% of D-glucose and 0.1% of 4-phenoxy-n-butyric acid ethyl ester and cultured at 30° C. with shaking at 125 strokes/minute, and after 67 hours, the bacterial cells were recovered by centrifugal separation, suspended again in 200 mL of a M9 culture medium containing 0.5% of D-glucose, 0.1% of 4-phenoxy-n-butyric acid ethyl ester and not containing inorganic nitrogen source (NH$_4$Cl), cultured at 30° C. with shaking at 125 strokes/minute, and after 21 hours, the bacterial cells were recovered by centrifugal separation, washed once with cold methanol and then freeze-dried.

The resulting freeze-dried pellets were suspended in 20 mL of chloroform and stirred at 60° C. for 24 hours to extract PHA. After being filtered through a membrane filter of 0.45 μm pore diameter, the extracted solution was concentrated in a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass spectrum analyzer (GC-MS, Shimadzu QP-5050, EI method) to identify the methyl ester of the PHA monomer unit. As a result, as shown in Table 3, it was confirmed that PHA containing 3-hydroxy-4-phenoxy-n-butyric acid as a monomer unit was produced.

TABLE 3

| Strain | YN2 |
|---|---|
| Cell dried weight (mg/L) | 1945 |
| Polymer dried weight (mg/L) | 4 |
| Polymer dried weight/cell dried weight | 2% |
| monomer unit composition(GC-MS: TIC peak area ratio) | |
| 3-hydroxybutyric acid | 13% |
| 3-hydroxyhexanoic acid | 2% |
| 3-hydroxyheptanoic acid | 3% |
| 3-hydroxyoctanoic acid | 9% |
| 3-hydroxynonanoic acid | 7% |
| 3-hydroxydecanoic acid | 27% |
| 3-hydroxydodecanoic acid | 9% |

TABLE 3-continued

| Strain | YN2 |
| --- | --- |
| 3-hydroxydodecenoic acid | 17% |
| 3-hydroxy-4-phenoxy-n-butyric acid | 13% |

Example 4

Either one of *Pseudomonas cichorii* H45 and *Pseudomonas jessenii* P161 was inoculated into 200 mL of a M9 culture medium containing 0.5% of D-glucose and 0.1% of 4-phenoxy-n-butyric acid ethyl ester and cultured at 30° C. with shaking at 125 strokes/minute, and after 45 hours, the bacterial cells were recovered by centrifugal separation, suspended again in 200 mL of a M9 culture medium containing 0.5% of D-glucose, 0.1% of 4-phenoxy-n-butyric acid ethyl ester and not containing inorganic nitrogen source (NH$_4$Cl), cultured at 30° C. with shaking at 125 strokes/minute, and after 40 hours, the bacterial cells were recovered by centrifugal separation, washed once with cold methanol and then freeze-dried.

The resulting freeze-dried pellets were suspended in 20 mL of chloroform and stirred at 60° C. for 24 hours to extract PHA. After being filtered through a membrane filter of 0.45 µm pore diameter, the extracted solution was concentrated in a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass spectrum analyzer (GC-MS, Shimadzu QP-5050, EI method) to identify the methyl ester of the PHA monomer unit. As a result, as shown in Table 4, it was confirmed that PHA containing 3-hydroxy-4-phenoxy-n-butyric acid as a monomer unit was produced.

TABLE 4

| Strain | H45 | P161 |
| --- | --- | --- |
| Cell dried weight (mg/L) | 1255 | 2230 |
| Polymer dried weight (mg/L) | 4 | 11 |
| Polymer dried weight/cell dried weight | 3% | 5% |
| Monomer unit composition(GC-MS: TIC peak area ratio) | | |
| 3-hydroxybutyric acid | 0% | 81% |
| 3-hydroxyoctanoic acid | 31% | 4% |
| 3-hydroxydecanoic acid | 45% | 5% |
| 3-hydroxydodecanoic acid | 24% | 1% |
| 3-hydroxy-4-phenoxy-n-butyric acid | 0% | 9% |

Example 5

*Pseudomonas cichorii* YN2 was inoculated into 200 mL of a M9 culture medium containing 0.5% of D-glucose and 0.01% of 4-phenoxy-n-butyric acid ethyl ester and cultured at 30° C. with shaking at 125 strokes/minute, and after 48 hours, the bacterial cells were recovered by centrifugal separation, suspended again in 200 mL of a M9 culture medium containing 0.5% of D-glucose, 0.1% of 4-phenoxy-n-butyric acid ethyl ester and not containing inorganic nitrogen source (NH$_4$Cl), cultured at 30° C. with shaking at 125 strokes/minute, and after 42 hours, the bacterial cells were recovered by centrifugal separation, washed once with cold methanol and then freeze-dried.

The resulting freeze-dried pellets were suspended in 20 mL of chloroform and stirred at 60° C. for 28 hours to extract PHA. After being filtered through a membrane filter of 0.45 µm pore diameter, the extracted solution was concentrated in a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass spectrum analyzer (GC-MS, Shimadzu QP-5050, EI method) to identify the methyl ester of the PHA monomer unit. As a result, as shown in Table 5, it was confirmed that PHA containing 3-hydroxy-4-phenoxy-n-butyric acid as a monomer unit was produced.

TABLE 5

| Strain | YN2 |
| --- | --- |
| Cell dried weight (mg/L) | 508 |
| Polymer dried weight (mg/L) | 27 |
| Polymer dried weight/cell dried weight | 5% |
| monomer unit composition(GC-MS: TIC peak area ratio) | |
| 3-hydroxyhexanoic acid | 1% |
| 3-hydroxyoctanoic acid | 5% |
| 3-hydroxynonanoic acid | 1% |
| 3-hydroxydecanoic acid | 13% |
| 3-hydroxydodecanoic acid | 5% |
| 3-hydroxydodecenoic acid | 7% |
| 3-hydroxy-4-phenoxy-n-butyric acid | 62% |

Example 6

*Pseudomonas cichorii* YN2 was inoculated into 200 mL of a M9 culture medium containing 0.5% of D-glucose and cultured at 30° C. with shaking at 125 strokes/minute, and after 48 hours, the bacterial cells were recovered by centrifugal separation, suspended again in 200 mL of a M9 culture medium containing 0.5% of D-glucose, 0.1% of 4-phenoxy-n-butyric acid ethyl ester and not containing inorganic nitrogen source (NH$_4$Cl), cultured at 30° C. with shaking at 125 strokes/minute. After 42 hours, the bacterial cells were recovered by centrifugal separation, washed once with cold methanol and then freeze-dried.

The resulting freeze-dried pellets were suspended in 20 mL of chloroform and stirred at 60° C. for 28 hours to extract PHA. After being filtered through a membrane filter of 0.45 µm pore diameter, the extracted solution was concentrated in a rotary evaporator and the concentrated solution was precipitated again in cold methanol and further only the precipitate was recovered and vacuum dried to obtain PHA. After being subjected to methanolysis by a common method, the obtained PHA was analyzed by a gas chromatography mass spectrum analyzer (GC-MS, Shimadzu QP-5050, EI method) to identify the methyl ester of the PHA monomer unit. As a result, as shown in Table 6, it was confirmed that PHA containing 3-hydroxy-4-phenoxy-n-butyric acid as a monomer unit was produced.

TABLE 6

| Strain | YN2 |
| --- | --- |
| Cell dried weight (mg/L) | 476 |
| Polymer dried weight (mg/L) | 27 |
| Polymer dried weight/cell dried weight | 6% |
| monomer unit composition(GC-MS: TIC peak area ratio) | |
| 3-hydroxybutyric acid | 6% |
| 3-hydroxyhexanoic acid | 1% |
| 3-hydroxyoctanoic acid | 11% |
| 3-hydroxydecanoic acid | 24% |

TABLE 6-continued

| Strain | YN2 |
|---|---|
| 3-hydroxydodecanoic acid | 11% |
| 3-hydroxydodecenoic acid | 15% |
| 3-hydroxytetradecenoic acid | 3% |
| 3-hydroxy-5-phenylvaleric acid | 10% |
| 3-hydroxy-4-phenoxy-n-butyric acid | 18% |

What is claimed is:

1. A production method of a polyhydroxyalkanoate comprising a monomer unit having the following chemical formula (2):

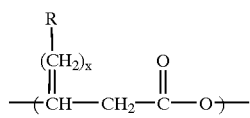  (2)

wherein R represents an arbitrarily selected substituent and x represents an integer of 0 to 8,
wherein the polyhydroxyalkanoate production method comprises a step of culturing a microorganism in a culture medium containing a substituted fatty acid ester having the following chemical formula (1):

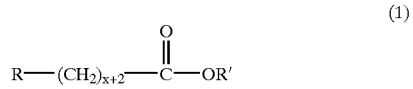  (1)

wherein R and R' separately represent an arbitrarily selected substituent and x represents an integer of 0 to 8,
wherein if R is H, x is not 1 or 2 in chemical formulas (1) and (2),
the microorganism being capable of taking the substituted fatty acid ester into its cells and synthesizing the polyhydroxyalkanoate in the culture medium,
wherein the polyhydroxyalkanoate production method further comprises a step of isolating the polyhydroxyalkanoate produced by the microorganism.

2. The production method according to claim 1, wherein said substituted fatty acid ester of the chemical formula (1) is a substituted fatty acid ester having the following chemical formula (3):

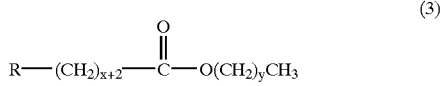  (3)

wherein R represents an arbitrarily selected substituent, x represents an integer of 0 to 8 and y represents an integer of 0 to 8.

3. The production method according to claim 2, wherein said substituted fatty acid ester of the chemical formula (1) is a substituted fatty acid ester having the following chemical formula (4):

  (4)

wherein R represents an arbitrarily selected substituent and x represents an integer of 0 to 8.

4. The production method according to claim 2, wherein said substituted fatty acid ester of the chemical formula (1) is a substituted fatty acid ester having the following chemical formula (5):

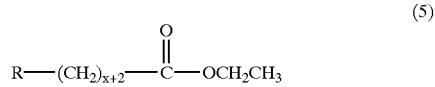  (5)

wherein R represents an arbitrarily selected substituent and x represents an integer of 0 to 8.

5. The production method according to any one of claims 3 or 4, wherein R in said chemical formulas (1) to (5) represents at least one of phenyl, phenoxy, benzoyl, cyclohexyl, thienyl, and chemically modified groups thereof.

6. The production method according to claim 4, wherein said substituted fatty acid ester represented by one of the chemical formulas (1) and (3) to (5) is at least one of 5-phenylvaleric acid methyl ester, 5-(4-fluorophenyl)valeric acid methyl ester, 6-phenylhexanoic acid methyl ester, 4-phenoxy-n-butyric acid methyl ester, 4-(3-fluorophenoxy)-n-butyric acid methyl ester, 4-(4-fluorophenoxy)-n-butyric acid methyl ester, 4-(4-cyanophenoxy)-n-butyric acid methyl ester, 4-(4-nitrophenoxy)-n-butyric acid methyl ester, 5-phenoxyvaleric acid methyl ester, 5-(4-fluorophenoxy)valeric acid methyl ester, 5-benzoylvaleric acid methyl ester, 4-cyclohexylbutyric acid methyl ester, 5-(2-thienyl)valeric acid methyl ester, 5-phenylvaleric acid ethyl ester, 5-(4-fluorophenyl)valeric acid ethyl ester, 6-phenylhexanoic acid ethyl ester, 4-phenoxy-n-butyric acid ethyl ester, 4-(3-fluorophenoxy)-n-butyric acid ethyl ester, 4-(4-fluorophenoxy)-n-butyric acid ethyl ester, 4-(4-cyanophenoxy)-n-butyric acid ethyl ester, 4-(4-nitrophenoxy)-n-butyric acid ethyl ester, 5-phenoxyvaleric acid ethyl ester, 5-(4-fluorophenoxy)valeric acid ethyl ester, 5-benzoylvaleric acid ethyl ester, 4-cyclohexylbutyric acid ethyl ester, and 5-(2-thienyl)valeric acid ethyl ester.

7. The production method according to claim 1, wherein the microorganism is cultured in two steps of culturing it in a culture medium containing the substituted fatty acid ester having said chemical formula (1) and a growth substrate and then culturing it in a culture medium containing the substituted fatty acid ester having said chemical formula (1) and a growth substrate in the absence of a nitrogen source.

8. The production method according to claim 1, wherein the microorganism is cultured only in one step of culturing the microorganism in a culture medium containing the substituted fatty acid ester having said chemical formula (1) and a growth substrate.

9. The production method according to claim 7, wherein said growth substrate is glucose.

10. The production method according to claim 1, wherein said microorganism belongs to *Pseudomonas* sp.

11. The production method according to claim 10, wherein said microorganism is at least one strain selected from *Pseudomonas cichorii* YN2, FERM BP-7375, *Pseudomonas cichorii* H45, FERM BP-7374, and *Pseudomonas jessenii* P161, FERM BP-7376.

* * * * *

UNITED STATES PATENT AND TRADEMARK OFFICE
CERTIFICATE OF CORRECTION

PATENT NO. : 6,867,023 B2
DATED : March 15, 2002
INVENTOR(S) : Tsutomu Honma et al.

It is certified that error appears in the above-identified patent and that said Letters Patent is hereby corrected as shown below:

Title page,
Item [56], References Cited, OTHER PUBLICATIONS,
"Ritter, H., et al.," reference, "nonanoat )" should read -- nonanoate) --;
"Kim, et al. (first occurrence)," reference, "Obtain d" should read -- Obtained --;
"Kim, et al. (second occurrence)," reference, "Polym r" should read -- Polymer --;
"Fritzsch , t al;" should read -- Fritzsch, et al.;" --; "bact rial poly st r" should read -- bacterial polyester --; "ph nyl p ndant" should read -- phenyl pendant --; and "Makromol. Ch m." should read -- Macromol. Chem. --.
Item [57], ABSTRACT,
Line 6, "characters" should read -- character --.

Column 3,
Line 65, "works." should read -- work. --.

Column 4,
Line 11, "got" should read -- obtained --.

Column 8,
Line 38, "generally, and" should read -- generally, --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,867,023 B2
DATED : March 15, 2005
INVENTOR(S) : Tsutomu Honma et al.

It is certified that error appears in the above-identified patent and that said Letters Patent is hereby corrected as shown below:

Title page,
Item [56], References Cited, OTHER PUBLICATIONS,
"Ritter, H., et al.," reference, "nonanoat )" should read -- nonanoate) --;
"Kim, et al. (first occurrence)," reference, "Obtain d" should read -- Obtained --;
"Kim, et al. (second occurrence)," reference, "Polym r" should read -- Polymer --;
"Fritzsch , t al;" should read -- Fritzsch, et al.;" --; "bact rial poly st r" should read -- bacterial polyester --; "ph nyl p ndant" should read -- phenyl pendant --; and "Makromol. Ch m." should read -- Macromol. Chem. --.
Item [57], ABSTRACT,
Line 6, "characters" should read -- character --.

Column 3,
Line 65, "works." should read -- work. --.

Column 4,
Line 11, "got" should read -- obtained --.

Column 8,
Line 38, "generally, and" should read -- generally, --.

This certificate supersedes Certificate of Correction issued February 28, 2006.

Signed and Sealed this

Fourth Day of April, 2006

JON W. DUDAS
*Director of the United States Patent and Trademark Office*